United States Patent
Biederman et al.

(10) Patent No.: US 10,201,297 B1
(45) Date of Patent: Feb. 12, 2019

(54) CAPACITIVE SENSING USING A CONTACT LENS SENSOR

(71) Applicant: Verily Life Sciences LLC, Mountain View, CA (US)

(72) Inventors: William James Biederman, Fox Island, WA (US); Daniel James Yeager, Berkeley, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 585 days.

(21) Appl. No.: 14/727,620

(22) Filed: Jun. 1, 2015

(51) Int. Cl.
*A61B 5/145* (2006.01)
*A61B 5/1477* (2006.01)
*A61B 5/00* (2006.01)

(52) U.S. Cl.
CPC ........ *A61B 5/14532* (2013.01); *A61B 5/0022* (2013.01); *A61B 5/1477* (2013.01); *A61B 5/6821* (2013.01); *A61B 5/746* (2013.01); *A61B 2560/0228* (2013.01)

(58) Field of Classification Search
CPC . A61B 5/14532; A61B 5/0022; A61B 5/6821; A61B 5/1477; A61B 5/746; A61B 2560/0228
See application file for complete search history.

(56) References Cited

U.S. PATENT DOCUMENTS

| | | | |
|---|---|---|---|
| 8,608,310 B2 | 12/2013 | Otis et al. | |
| 8,870,370 B1 | 10/2014 | Otis et al. | |
| 2011/0028807 A1 | 2/2011 | Abreu | |
| 2014/0240655 A1 | 8/2014 | Pugh et al. | |
| 2015/0057516 A1 | 2/2015 | Mujeb-U-Rahman et al. | |
| 2017/0042480 A1* | 2/2017 | Gandhi | G02C 7/04 |

OTHER PUBLICATIONS

Smith, Wirelessly Powered Sensor Networks and Computational RFID, Springer, 2013, p. 53.*

* cited by examiner

*Primary Examiner* — Tiffany Weston
*Assistant Examiner* — Tho Tran
(74) *Attorney, Agent, or Firm* — McDonnell Boehnen Hulbert & Berghoff LLP (57) ABSTRACT

Systems and methods are described that relate to a device, such as an eye-mountable device. The eye-mountable device may include a capacitance sensor and associated circuitry configured to measure a capacitance and/or a change in capacitance based on a material being in proximity with the capacitance sensor. For example, the capacitance sensor and associated circuitry may be operable to detect an eye-related movement of a wearer of the eye-mountable device. The eye-related movement may be a blink, a wink, an eye moving with respect to an eyelid, an eyelid moving with respect to the capacitance sensor, or an eyelid closing. At least one sensor electrode of the capacitance sensor may operable to carry out an additional function, e.g. to measure a level of glucose in tear-fluid or to provide wireless communication.

12 Claims, 7 Drawing Sheets

CAPACITIVE SENSING USING A CONTACT LENS SENSOR

BACKGROUND

Unless otherwise indicated herein, the materials described in this section are not prior art to the claims in this application and are not admitted to be prior art by inclusion in this section.

Certain medical conditions or states can be characterized by slow changes of a physiological property (e.g., a blood glucose concentration) over long periods of time and/or by infrequent, short-timescale events. Such physiological properties can be measured periodically (e.g., by periodically accessing blood of a person). An implanted or wearable device could be employed to provide continuous or near-continuous measurement of such physiological properties. Such implantable or wearable devices can be battery powered and/or powered by radio frequency energy or other wireless energy sources. Further, such devices can be configured to indicate measured physiological properties wirelessly (e.g., by using an RFID antenna and transmitter, by using a Bluetooth antenna and transmitter).

SUMMARY

In a first aspect, an eye-mountable device is provided. The eye-mountable device includes a substrate, a capacitance sensor disposed proximate to the substrate, and a controller disposed proximate to the substrate. The substrate is at least partially embedded within a shaped polymeric material. The capacitance sensor includes at least two sensor electrodes. At least one sensor electrode of the at least two sensor electrodes is operable to carry out an additional function. The controller is communicatively coupled to the at least two sensor electrodes. The controller is configured to receive data indicative of a change in mutual capacitance between the at least two sensor electrodes. The controller is further configured to detect an eye-related movement based on the change in mutual capacitance being greater than a threshold capacitance. The controller is also configured to, in response to detecting the eye-related movement, produce a signal.

In a second aspect, a method is provided. The method includes receiving data indicative of a change in mutual capacitance between at least two sensor electrodes of a capacitance sensor. At least one sensor electrode of the at least two sensor electrodes is operable to carry out an additional function. The capacitance sensor is disposed proximate to a substrate. The substrate is at least partially embedded within a shaped polymeric material. The shaped polymeric material is configured to be mounted proximate to an eye. The method also includes detecting an eye-related movement based on the change in mutual capacitance being greater than a threshold capacitance. The method further includes, in response to detecting the eye-related movement, producing a signal.

Other aspects, embodiments, and implementations will become apparent to those of ordinary skill in the art by reading the following detailed description, with reference where appropriate to the accompanying drawings.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

Overview

An eye-mountable device may include a capacitance sensor and associated circuitry configured to measure a capacitance and/or a change in capacitance based on a material being in proximity with the capacitance sensor. For example, the capacitance sensor and associated circuitry may be operable to detect an eye-related movement of a wearer of the eye-mountable device. The eye-related movement may be a blink, a wink, an eye moving with respect to an eyelid, an eyelid moving with respect to the capacitance sensor, or an eyelid closing.

In an example embodiment, the eye-mountable device may include a flexible substrate similar to a contact lens. The eye-mountable device may be configured to be worn proximate to an eye. The capacitance sensor may be configured as a pair of interdigitated electrodes.

In an example embodiment, at least one sensor electrode of the capacitance sensor may be operable to carry out an additional function. For example, at least one of the electrodes of the capacitance sensor may be configured to provide a wireless communication function. As such, at least one sensor electrode of the capacitance sensor may include a loop antenna further configured to transmit and/or receive signals.

Additionally or alternatively, the at least one sensor electrode of the capacitance sensor may be operable to sense a presence of an analyte of interest. For instance, the at least one sensor electrode may be a working electrode or a reference electrode of an electrochemical sensor. Optionally, the eye-mountable device may be configured to measure an analyte of interest in the body with the capacitance sensor or a different sensor proximate to the eye-mountable device. In some embodiments, such a sensor may be operable to measure a level of glucose in tear-fluid.

The capacitance sensor may be configured to have a higher capacitance between the electrodes when an eyelid of a wearer of the head-mountable device is closed as compared to when the eyelid is open. A controller may receive information indicative of a capacitance change. Based on the information, the controller may determine or detect an eye-related movement.

In response to the controller detecting or determining the eye-related movement, a signal may be generated. The signal may serve to trigger an action related to a function of the eye-mountable device or another device. For instance, the signal indicative of the eye-related movement may trigger or cause: 1. an acknowledgement of an alarm condition; 2. a display to illuminate based on an analyte level; or 3. an indication of moisture level in the eye.

Other functions local to or remote from the eye-mountable device may be triggered by the signal. For example, the detection of an eye-related movement may be useful to trigger an electrochemical sensor reading of a glucose level or to trigger another type of sensor reading or action. For example, a detected eye-related movement may cause a display to indicate a measured value, which may relate to a value of the analyte measured by the electrochemical sensor. Alternatively, detection of an eye-related movement may trigger a communication signal to other components of the eye-mountable device and/or to another device. Furthermore, the capacitance sensor or different sensor may be operable to detect a moisture level of the eye, e.g. dryness of an eye. Other functions are contemplated.

A calibration of the device may be performed to record information relating to at least an open eyelid state and a closed eyelid state. The calibration of the device may help to eliminate anatomical variables, which may differ by individual. The calibration of the device may be performed initially when a user mounts the eye-mountable device on his/her eye. Alternatively, calibration may be performed based on historical and/or statistical analysis of past capacitance measurements. Other ways to calibrate the device are possible.

System Examples

Figure 1:
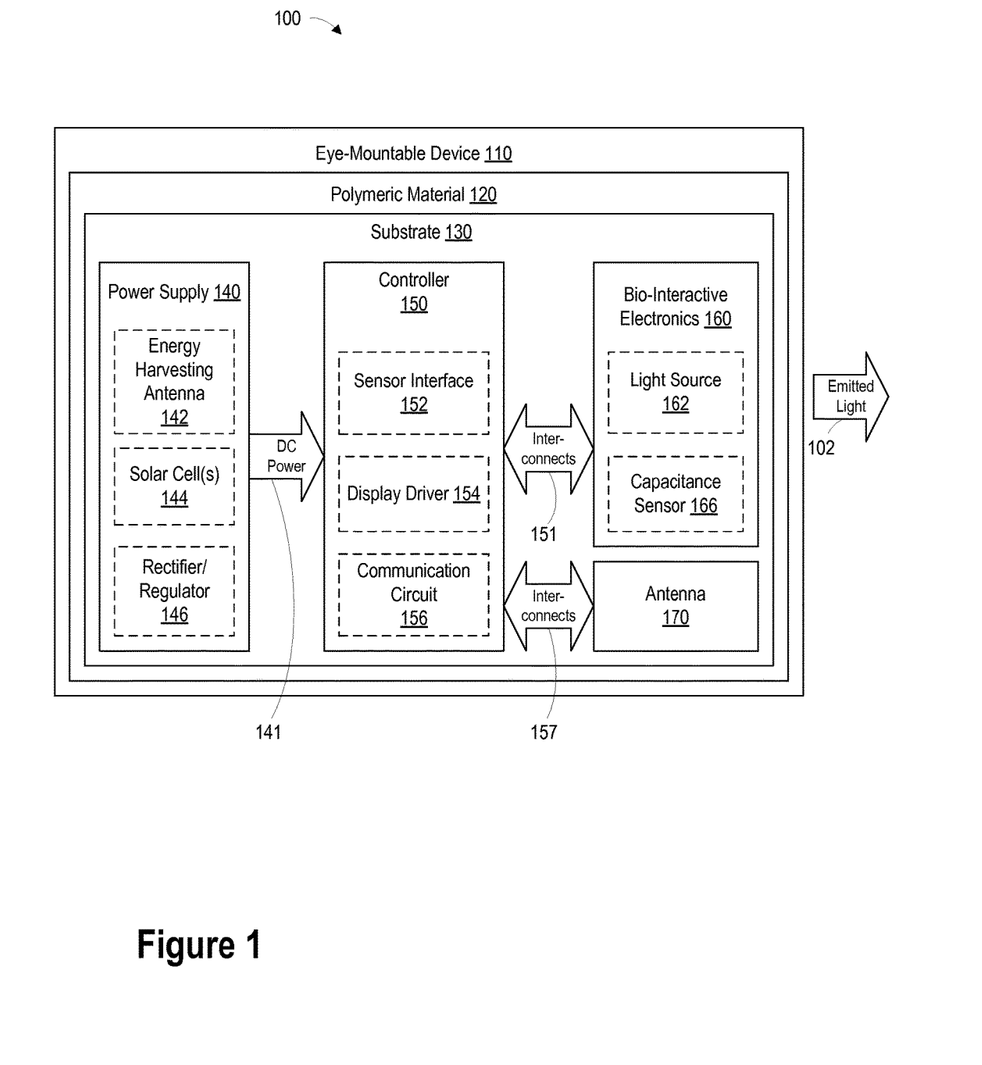
FIG. 1 is a block diagram of an eye-mountable device according to an example embodiment.

FIG. 1 is a block diagram of an eye-mountable device 110 according to an example embodiment. The exposed regions of the eye-mountable device 110 are made of a polymeric material 120 formed to be contact-mounted to a corneal surface of an eye. A substrate 130 is embedded in the polymeric material 120 to provide a mounting surface for a power supply 140, a controller 150, bio-interactive electronics 160, and an antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110 (e.g., to communicate with an external device). The antenna 170, the controller 150, the power supply 140, and the bio-interactive electronics 160 can all be situated on the embedded substrate 130. Alternatively, one or more of the elements of the eye-mountable device 110 may be situated on a plurality of substrates 130 embedded within the polymeric material 120. Because the eye-mountable device 110 includes electronics and is configured to be contact-mounted to an eye, it is also referred to herein as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eyelid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some instances, the polymeric material 120 can be a deformable ("non-rigid") material to enhance wearer comfort. In some instances, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on the substrate 130 to form circuitry, electrodes, etc. For example, the antenna 170 can be formed by depositing a pattern of gold or another conductive material on the substrate 130. Similarly, interconnects 151, 157 between the controller 150 and the bio-interactive electronics 160, and between the controller 150 and the antenna 170, respectively, can be formed by depositing suitable patterns of conductive materials on the substrate 130. A combination of microfabrication techniques including, without limitation, the use of photoresists, masks, etching techniques, deposition techniques, and/or plating techniques can be employed to pattern materials on the substrate 130. The substrate 130 can be a relatively rigid material, such as polyethylene terephthalate ("PET"), parylene, or another material sufficient to structurally support the circuitry and/or electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from the center of the eye-mountable device 110 and thereby avoid interference with light transmission to the eye through the center of the eye-mountable device 110. For example, where the eye-mountable device 110 is shaped as a concave-curved disk, the substrate 130 can be embedded around the periphery (e.g., near the outer circumference) of the disk. In some embodiments, the bio-interactive electronics 160 (and the substrate 130) can be positioned in the center region of the eye-mountable device 110. The bio-interactive electronics 160 and/or substrate 130 can be substantially transparent to incoming visible light to mitigate interference with light transmission to the eye. Thus, some or all of the bio-interactive electronics 160, e.g. light source 162, may optionally be positioned in the center of the eye-mountable device so as to generate perceivable visual cues to a wearer of the eye-mountable device 110, such as by displaying information via the light source 162.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

The power supply 140 is configured to harvest energy to power the controller 150 and bio-interactive electronics 160. For example, a radio-frequency energy-harvesting antenna 142 can capture energy from incident radio radiation, for example, from an external device. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate with an external device. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such as a sensor 166, in bio-interactive electronics 160 to obtain input from the biological environment (e.g., from a portion of subsurface vasculature in the biological environment and/or from an environment local to the eye-mountable device 110). Additionally or alternatively, the interaction could involve the use of one or more components, such as light source 162, to provide an output to the biological environment, e.g. in the form of emitted light 102.

The controller 150 can optionally include a display driver module 154 for operating light source 162. Light source 162 may include liquid crystal technologies, microelectromechanical technologies, emissive diode technologies, etc. to selectively transmit, reflect, and/or emit light according to information from the display driver module 154. Such a light source 162 may also optionally include more than one color (e.g., red, green, and blue pixels) to render visual content in color. Furthermore, light source 162 may include a plurality of light sources. In such a scenario, the display driver module 154 may include, for example, one or more data lines providing programming information to separately programmed pixels in the light source 162 and one or more addressing lines for setting groups of pixels to receive such programming information. Such a light source 162 situated near an eye of a wearer of the eye-mountable device 110 may also include one or more lenses to direct light from the pixel array to a focal plane perceivable by the eye.

In one example, the controller 150 includes a sensor interface module 152 that is configured to receive data from capacitance sensor 166. Based on the data received by the sensor interface module 152, the display driver 154 may cause the light source 162 to generate an indication related to information received from the capacitance sensor 166.

In an example embodiment, capacitance sensor 166 may include at least two sensor electrodes. For example, the capacitance sensor 166 can be an amperometric sensor that includes a working electrode and a reference electrode. In an example embodiment, capacitance sensor 166 may be configured to sense a capacitance between the working and reference electrodes. Additionally or alternatively, the capacitance sensor 166 may be configured to carry out an additional function. For example, the additional function may include sensing a concentration of one or more analytes, e.g. glucose, from tear fluid proximate to an eye.

In an example embodiment, a voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

In response to the capacitance sensor 166 detecting an abnormally high glucose level, controller 150 and/or the sensor interface module 152 may cause the light source 162 to provide an alert indication. The alert indication may include a flashing light, a constant light, and/or a predetermined pattern or series of flashing lights. Other indications are possible, including but not limited to different color lights (e.g. red, yellow, red) or other indications configured to provide a user of the eye-mountable device 110 with information about the user's biological environment and/or physiological condition. Additionally or alternatively, one or more electronic elements or systems configured to operate the light source 162 could be disposed as part of the bio-interactive electronics 160 (e.g., by being formed from the same integrated circuit or semiconductor wafer as the light source 162) or as part of some other aspect of the eye-mountable device 110.

The light source 162 may be disposed such that light is directly or indirectly viewable by a user of the eye-mountable device 110. As such, the light source 162 may be disposed so as to be visible from the concave side of the eye-mountable device. The eye-mountable device 110 could include multiple light sources configured to provide a plurality of different indications based on physiological data received by, e.g., the capacitance sensor 166. The eye-mountable device 110 could include filters, mirrors, lenses, diffraction gratings, or other optical elements configured to focus, block, or otherwise modify light provided by the light source 162.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivably by an external reader (not shown). For example, the communication circuit 156 can cause variations in the amplitude, phase, and/or frequency of backscatter radiation from the antenna 170, which may be detected by the external reader.

The external reader may be a smart phone, digital assistant, or other portable computing device configured to be in wireless communication with the eye-mountable device 110 via a wireless communication link. The external reader may also be implemented as an antenna module that can be plugged into a portable computing device. In some instances, the external reader may be a special-purpose device configured to be worn relatively near a wearer's eye. For example, the external reader may be integrated in a piece of jewelry such as a necklace, earring, etc. or integrated in an article of clothing worn near the head, such as a hat, headband, etc. The external reader may additionally or alternatively be implemented in eye glasses or a head-mounted display.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical feature. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided on a chip by a rectifier and/or regulator components on the same chip. That is, the functional blocks in FIG. 1 shown as the power supply block 140 and controller block 150 need not be implemented as separated modules. Moreover, one or more of the functional modules described in FIG. 1 can be implemented by separately packaged chips electrically connected to one another.

Additionally or alternatively, the energy harvesting antenna 142 and the communication antenna 170 may be implemented with the same physical antenna. For example, a loop antenna can both harvest incident radiation for power generation and communicate information via backscatter radiation.

As described above, the capacitance sensor 166 may be operable to carry out the additional function of sensing an analyte. Specifically, the capacitance sensor 166 may provide information indicative of a concentration of glucose in tear fluid proximate to the eye-mountable device 110. Furthermore, in an example embodiment, the capacitance sensor 166 is configured to sense an eye-related movement of a wearer of the eye-mountable device 110. For example, when the eye-mountable device 110 is worn proximate to an eye, the capacitance sensor 166 may be operable to provide a change in capacitance in response to an eyelid moving near the capacitance sensor 166. As an illustrative example, the capacitance sensor 166 may be configured to have a higher capacitance between electrodes of the capacitance sensor 166 when the eyelid of a wearer of the eye-mountable device 110 is open, compared to when the eyelid of the wearer is closed. In such a scenario, the controller 150 and/or the sensor interface 152 may be configured to receive data indicative of a change in mutual capacitance between the sensor electrodes. Further, the controller 150 may be configured to detect or determine an eye-related movement based on the change in mutual capacitance being greater than a threshold capacitance difference. In response to detecting the eye-related movement, the controller 150 may be configured to produce a signal.

In some embodiments, the signal may cause the controller 150 and/or other components of the eye-mountable device 110 to perform functions. For example, in response to the signal, the controller 150 may cause the sensor interface 152 to sample data from the capacitance sensor 166. As such, a detected eye-related movement may trigger an analyte sample.

In another example embodiment, in the case when a notification is being provided to a user (e.g. a high glucose alert indication), an eye-related movement detected via capacitance sensor 166 may cause the controller 150 and/or the display driver 154 to stop the notification. In other words, a detected eye-related movement may trigger a dismissal of the alert indication.

Figure 2A:
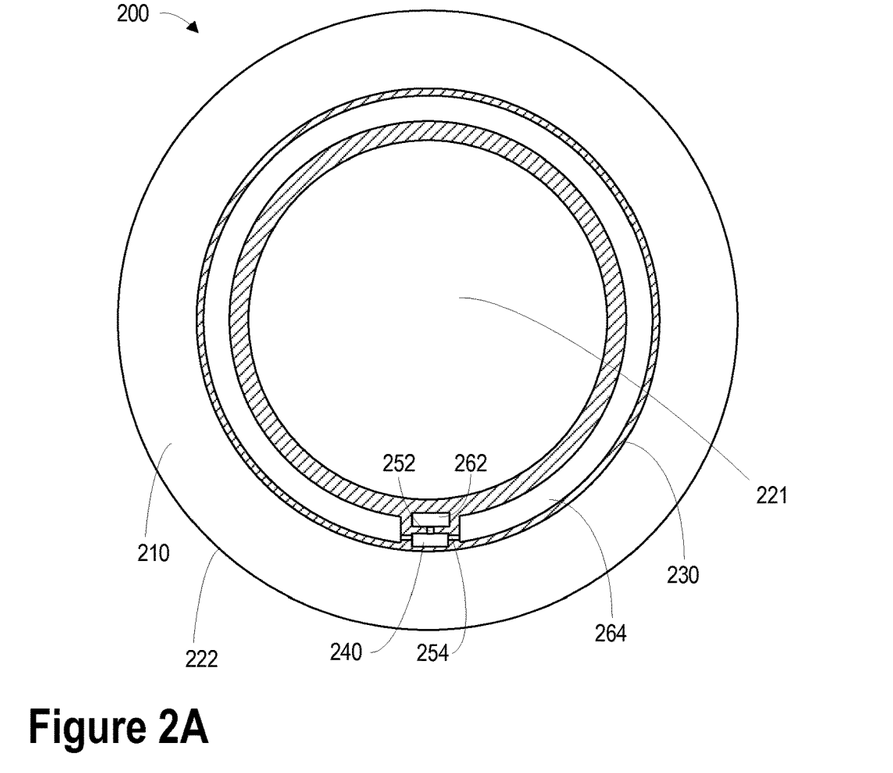
FIG. 2A is a top view of an eye-mountable device according to an example embodiment.
Figure 2B:
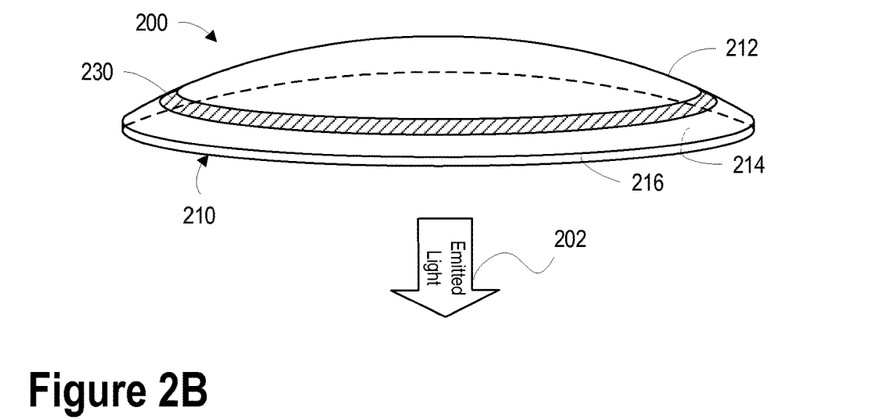
FIG. 2B is an aspect view of the example eye-mountable device shown in FIG. 2A according to an example embodiment.

FIG. 2A is a bottom view of an example eye-mountable electronic device 200 according to an example embodiment. FIG. 2B is an aspect view of the example eye-mountable electronic device 200 shown in FIG. 2A according to an example embodiment. It is noted that relative dimensions in FIGS. 2A and 2B are not necessarily to scale, but have been rendered for purposes of explanation only in describing the arrangement of the example eye-mountable electronic device 200. The eye-mountable device 200 is formed of a polymeric material 210 shaped as a curved disk. The polymeric material 210 may be a substantially transparent material to allow incident light to be transmitted to the eye while the eye-mountable device 200 is mounted to the eye. The polymeric material 210 can be a biocompatible material similar to those employed to form vision correction and/or cosmetic contact lenses in optometry, such as polyethylene terephthalate ("PET"), polymethyl methacrylate ("PMMA"), silicones, silicone hydrogels, combinations of these, etc. The polymeric material 210 can be formed with one side having a concave surface 214 suitable to fit over a corneal surface of an eye. The opposing side of the disk can have a convex surface 212 that does not interfere with eyelid motion while the eye-mountable device 200 is mounted to the eye. A circular outer side edge 216 connects the concave surface 214 and convex surface 212.

The eye-mountable device 200 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 200 can be selected according to the size and/or shape of the corneal surface of the wearer's eye.

The polymeric material 210 can be formed with a curved shape in a variety of ways. For example, techniques similar to those employed to form vision-correction contact lenses, such as heat molding, injection molding, spin casting, etc. can be employed to form the polymeric material 210. While the eye-mountable device 200 is mounted in an eye, the convex surface 212 faces outward to the ambient environment while the concave surface 214 faces inward, toward the corneal surface. The convex surface 212 can therefore be considered an outer, top surface of the eye-mountable device 210 whereas the concave surface 214 can be considered an inner, bottom surface. The "bottom" view shown in FIG. 2A is facing the concave surface 214. From the bottom view shown in FIG. 2A, the outer periphery 222, near the outer circumference of the curved disk is curved out of the page, whereas the center region 221, near the center of the disk may be considered substantially parallel to the page.

A substrate 230 is embedded in the polymeric material 210. The substrate 230 can be embedded to be situated along the outer periphery 222 of the polymeric material 210, away from the center region 221. The substrate 230 does not interfere with vision because it is too close to the eye to be in focus and is positioned away from the center region 221 where incident light is transmitted to the eye-sensing portions of the eye. Moreover, the substrate 230 can be formed of a transparent material to further mitigate any effects on visual perception.

The substrate 230 can be shaped as a flat, circular ring (e.g., a disk with a central hole). The flat surface of the substrate 230 (e.g., along the radial width) is a platform for mounting electronics such as chips (e.g., via flip-chip mounting) and for patterning conductive materials (e.g., via deposition techniques) to form electrodes, antenna(e), and/or connections. The substrate 230 and the polymeric material 210 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented in a variety of different form factors.

A loop antenna 264, controller 240, and bio-interactive electronics 262 are disposed on the embedded substrate 230. The controller 240 may be a chip including logic elements configured to operate the bio-interactive electronics 262 and the loop antenna 264. The controller 240 is electrically connected to the loop antenna 264 by interconnects 254 also situated on the substrate 230. Similarly, the controller 240 is electrically connected to the bio-interactive electronics 262 by an interconnect 252. The interconnects 252, 254, the loop antenna 264, and any conductive electrodes (e.g., for an electrochemical sensor, a capacitance sensor, etc.) can be formed from conductive materials patterned on the substrate 230 by a process for precisely patterning such materials, such as deposition, lithography, lift-off, etching, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 2A, which is a view facing the convex surface 212 of the eye-mountable device 200, the bio-interactive electronics module 262 is mounted to a side of the substrate 230 facing the concave surface 214. Where the bio-interactive electronics module 262 includes a capacitance sensor (e.g. capacitance sensor 166 illustrated and described in reference to FIG. 1), for example, mounting such a capacitance sensor on the substrate 230 to be close to the concave surface 214 allows the capacitance sensor to sense analyte concentrations in tear film near the surface of the eye. However, the electronics, electrodes, etc. situated on the substrate 230 can be mounted to either the "inward" facing side (e.g., situated closest to the concave surface 214) or the "outward" facing side (e.g., situated closest to the convex surface 212). Moreover, in some embodiments, some electronic components can be mounted on one side of the substrate 230, while other electronic components are mounted to the opposing side, and connections between the two can be made via conductive materials passing through the substrate 230.

The loop antenna 264 can be a layer of conductive material patterned along the flat surface of the substrate to form a flat, or substantially flat, conductive ring. In some instances, the loop antenna 264 can be formed without making a complete loop. For instance, the antenna 264 can have a cutout to allow room for the controller 240 and bio-interactive electronics 262, as illustrated in FIG. 2A. However, the loop antenna 264 can also be arranged as a continuous strip of conductive material that wraps entirely around the flat surface of the substrate 230 one or more times. For example, a strip of conductive material with multiple windings can be patterned on the side of the substrate 230 opposite the controller 240 and bio-interactive electronics 262. Interconnects between the ends of such a wound antenna (e.g., the antenna leads) can be passed through the substrate 230 to the controller 240.

Figure 2C:
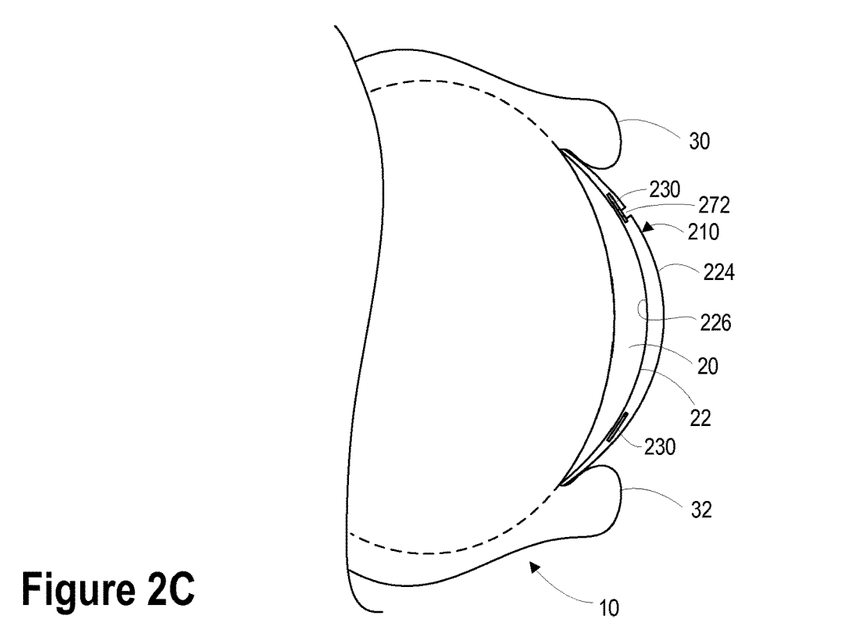
FIG. 2C is a side cross-section view of the example eye-mountable device shown in FIGS. 2A and 2B while mounted to a corneal surface of an eye according to an example embodiment.
Figure 2D:
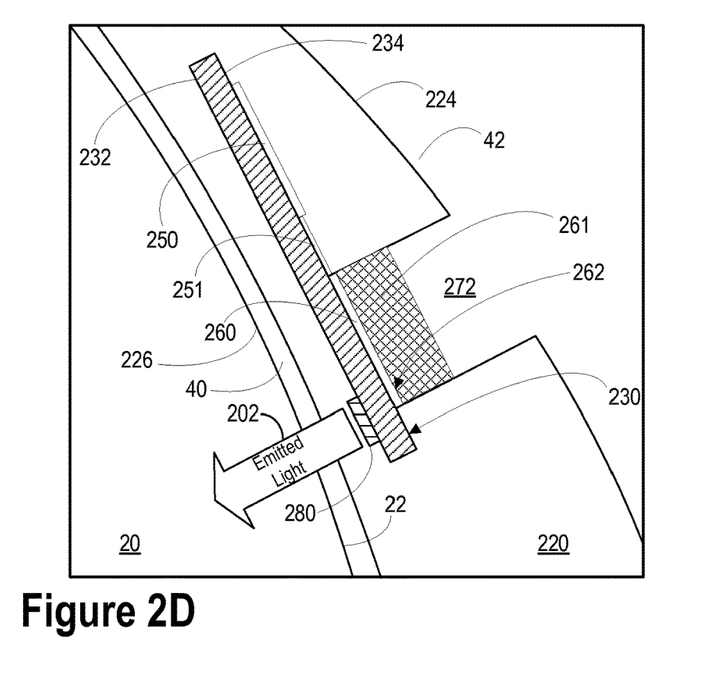
FIG. 2D is a side cross-section view of the example eye-mountable device when mounted as shown in FIG. 2C according to an example embodiment.

FIG. 2C is a side cross-section view of the example eye-mountable device 200 shown in FIGS. 2A and 2B while mounted to a corneal surface 22 of an eye 10 according to an example embodiment. FIG. 2D is a side cross-section view of the example eye-mountable device 200 when mounted as shown in FIG. 2C according to an example embodiment. It is noted that relative dimensions in FIGS. 2C and 2D are not necessarily to scale, but have been rendered for purposes of explanation only in describing the arrangement of the example eye-mountable electronic device 200. For example, the total thickness of the eye-mountable device can be about 200 micrometers, while the thickness of the tear film layers 40, 42 can each be about 10 micrometers, although this ratio may not be reflected in the drawings. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the eye-mountable device 200 is mounted in the eye 10, the tear film coats both the concave and convex surfaces 224, 226 with an inner layer 40 (along the concave surface 226) and an outer layer 42 (along the convex layer 224). The tear film layers 40, 42 may be about 10 micrometers in thickness and together account for about 10 microliters.

The tear film layers 40, 42 are distributed across the corneal surface 22 and/or the convex surface 224 by motion of the eyelids 30, 32. For example, the eyelids 30, 32 raise and lower, respectively, to spread a small volume of tear film across the corneal surface 22 and/or the convex surface 224 of the eye-mountable device 210. The tear film layer 40 on the corneal surface 22 also facilitates mounting the eye-mountable device 210 by capillary forces between the concave surface 226 and the corneal surface 22. In some embodiments, the eye-mountable device 210 can also be held over the eye in part by vacuum forces against corneal surface 22 due to the concave curvature of the eye-facing concave surface 226.

As shown in the cross-sectional views in FIGS. 2C and 2D, the substrate 230 can be inclined such that the flat mounting surfaces of the substrate 230 are approximately parallel to the adjacent portion of the concave surface 226. As described above, the substrate 230 is a flattened ring with an inward-facing surface 232 (closer to the concave surface 226 of the polymeric material 220) and an outward-facing surface 234 (closer to the convex surface 224). The substrate 230 can have electronic components and/or patterned conductive materials mounted to either or both mounting surfaces 232, 234. As shown in FIG. 2D, the bio-interactive electronics 260, controller 250, and conductive interconnect 251 are mounted on the outward-facing surface 234 such that the bio-interactive electronics 260 are relatively closer in proximity to the outer tear film layer 42 than if they were mounted on the inward-facing surface 232. With this arrangement, the bio-interactive electronics 260 can receive analyte concentrations in the outer tear film 42 through the channel 272. However, in other examples, the bio-interactive electronics 260 may be mounted on the inward-facing surface 232 of the substrate 230 such that the bio-interactive electronics 260 are facing the concave surface 226 and able to receive analyte concentrations from the inner tear film 40.

In an example embodiment, a light source 280 may be coupled to the inward-facing surface 232 of the substrate 230. The light source 280 may be similar or identical to the light source 162 illustrated and described in reference to FIG. 1. The light source 280 may be configured to provide emitted light 202, which may be observable by a wearer of the eye-mountable device 200. As described elsewhere herein, the emitted light 202 may provide information indicative of a notification and/or an alert, which may be based on a concentration of an analyte (e.g. glucose) being higher or lower than a predetermined range.

Figure 3A:
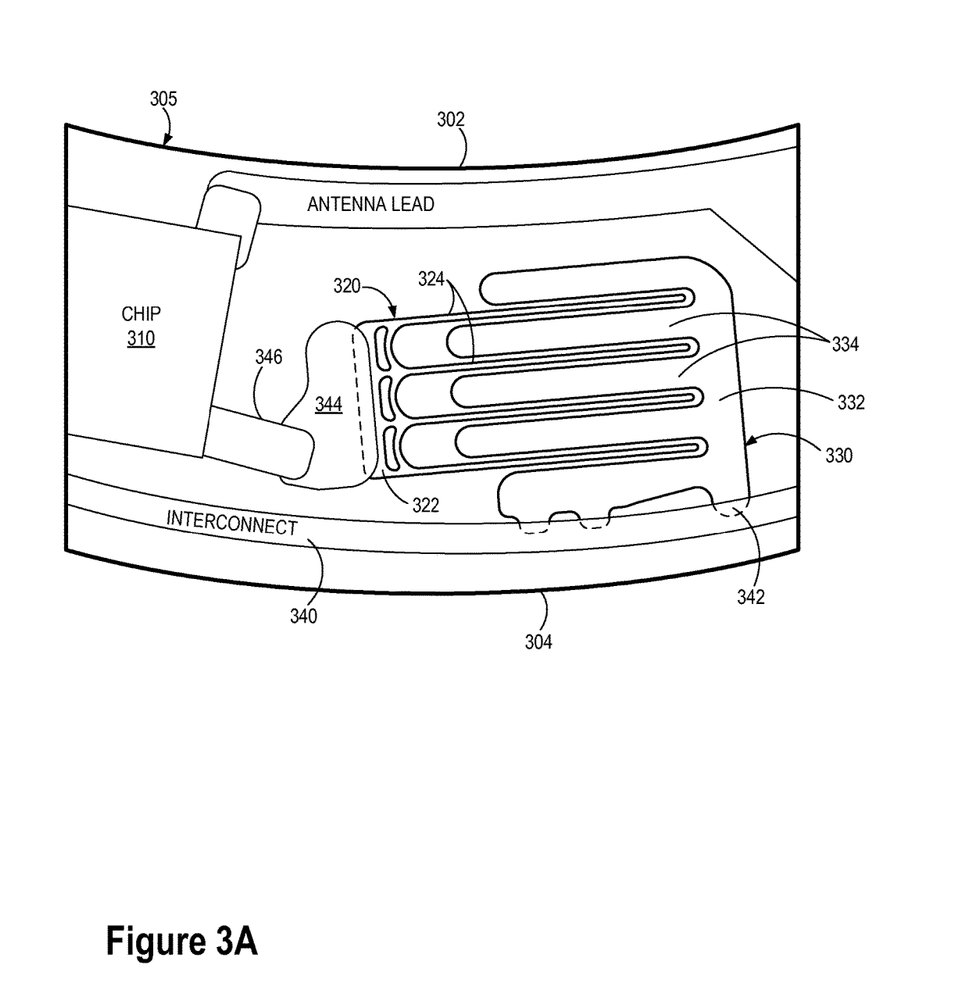
FIG. 3A illustrates an example arrangement for electrodes in an electrochemical sensor disposed on a surface of an eye-mountable device according to an example embodiment.

FIG. 3A illustrates an example arrangement for electrodes in an electrochemical sensor disposed on a surface of an eye-mountable device. FIG. 3A illustrates a portion of a substrate 305 on which the electrochemical sensor is mounted. The electrochemical sensor may be similar or identical to capacitance sensor 166 as illustrated and described in reference to FIG. 1. Furthermore, the capacitance sensor may share at least one sensor electrode of the electrochemical sensor. As such, the at least one electrode of the capacitance sensor may be operable to carry out multiple functions, such as capacitance sensing and analyte sensing, e.g. via electrochemical reactions.

The substrate 305 is configured to be embedded in an eye-mountable device and may be similar or identical to the substrate 230 described above in connection with FIGS. 2A-2B. The substrate 305 may be shaped as a flattened ring with an inner edge 302 and an outer edge 304. The two edges 302, 304 may both be at least approximately circular, although only a portion of each is shown in FIG. 3A.

The substrate 305 provides a mounting surface for mounting a chip 310 and for sensor electrodes, an antenna, and conductive interconnects between pads or terminals on the chip 310 and the other components. In an example embodiment, the electrochemical sensor includes a working electrode 320 and a reference electrode 330 disposed in an interdigitated arrangement. The working electrode 320 includes four fingers 324 that can each have a relatively narrow width (e.g., about 25 micrometers) and that extend from a base 322. The working electrode 320 is electrically connected to a connection pad of the chip 310 through a pair of overlapped interconnects 344, 346. The reference electrode 330 includes fingers 334 that extend from a base 332. As shown in FIG. 3A, the fingers 324, 334 of the two electrodes 320, 330 can be at least approximately parallel with one another. Moreover, the electrodes 320, 330 can be arranged in an interdigitated arrangement such that each of the fingers 324 of the working electrode 320 is interposed between two of the fingers 334 of the reference electrode in an at least approximately symmetric manner. As such, each of the working electrode fingers 324 has a similar voltage gradient along both opposing side edges. The reference electrode 330 can then be electrically connected to another pad (not visible) on the chip 310 via the interconnect 340 that connects to the reference electrode 330 at multiple overlap points 342.

The chip 310 can also be connected to other components via additional connection pads. For example, as shown in FIG. 3A, the chip 310 can be connected to an antenna lead, which can be formed of a patterned conductive material, such as electroplated gold, for example, that substantially circles the substrate 305 to create a loop antenna.

Figure 3B:
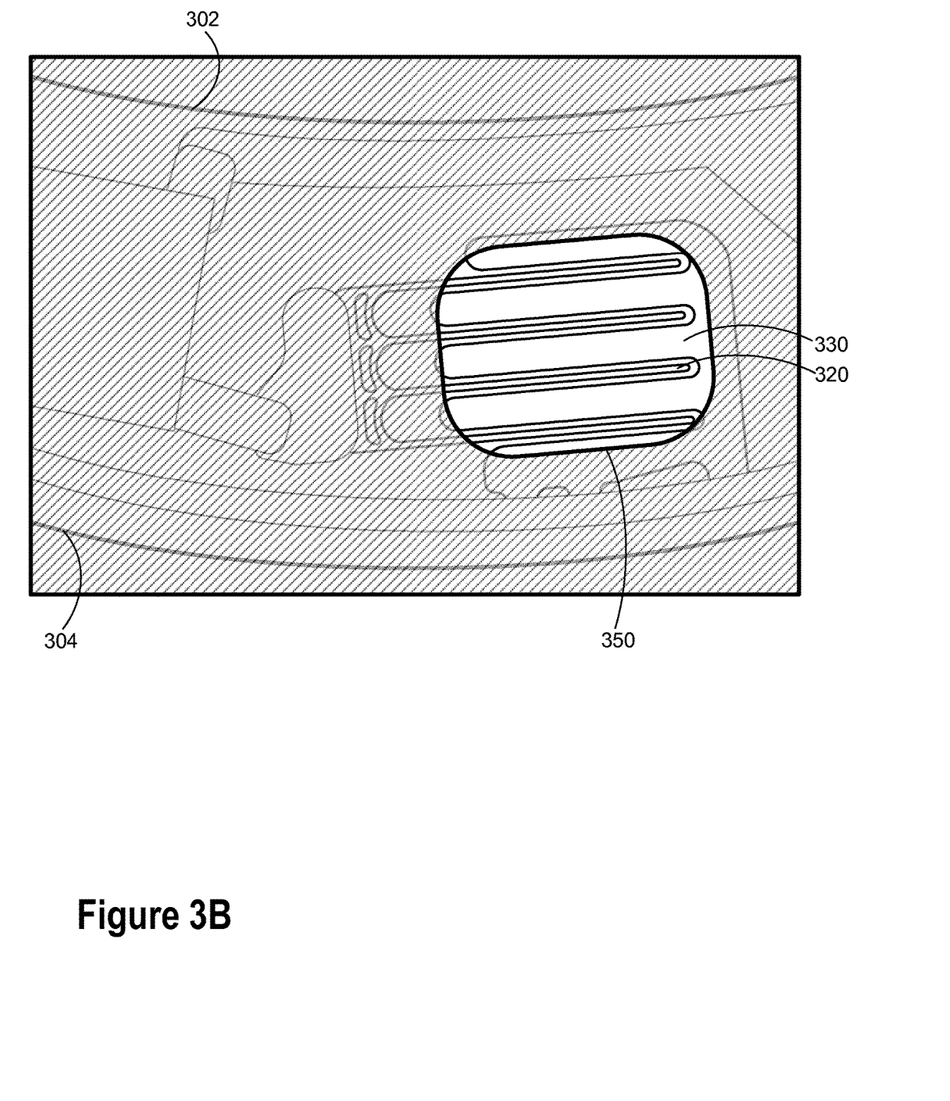
FIG. 3B illustrates the arrangement in FIG. 3A when embedded in a polymeric material with a channel positioned to expose the sensor electrodes according to an example embodiment.

FIG. 3B illustrates the arrangement in FIG. 3A when embedded in a polymeric material with a channel 350 positioned to expose the electrochemical sensor electrodes 320, 330. In FIG. 3B, the polymeric material is illustrated by the hash pattern that is superimposed over the portion of the substrate 305 shown in FIG. 3A. The channel 350 may be formed by removing a portion of the encapsulating polymeric material (e.g., by etching, by removing a layer defined by a photoresist, etc.). The channel 350 exposes a region including the electrochemical sensor electrodes 320, 330, such that tear film coating the polymeric material is able to contact the sensor electrodes 320, 330, and an analyte therein is able to electrochemically react at the electrodes. The exposed region created by the channel 350 can include a desired cumulative length of the working electrode 320 (e.g., a cumulative length of approximately 1000 micrometers). The exposed area of the reference electrode can be at least five times the exposed area of the working electrode, to ensure that the half-cell potential of the reference electrode is substantially stable while making amperometric measurements.

In the sensor electrode arrangement shown in FIG. 3A-3B in which the electrodes are mounted on the substrate 305, the extended fingers 324, 334 of the two electrodes 320, 330 are each oriented at least approximately tangential to the side edges 302, 304 of the substrate. In other words, the inter-digitated fingers 324, 334 have lengths that are locally parallel to the side edges 302, 304. As such, the electrodes 320, 330 are more able to comply with curvature in the substrate 305. Arranging the electrode fingers 344, 334 to be locally parallel to the side edges causes each of the electrode fingers 324, 334 to be located along a single radius of curvature, even as the substrate 305 conforms to a convex curvature of an eye-mountable device (or adjusts to stresses or strains of being contact-mounted to an eye). For example, if the substrate 305 is curved to comply with the concave curvature of an eye-mountable device in which the substrate 305 is embedded, the individual finger extensions 324, 334 can conform to the local radius of curvature at each location without substantially influencing the inter-electrode spacing. By contrast, an arrangement with finger extensions that cross multiple radii of curvature may be urged to adjust its inter-electrode spacing in a non-uniform manner, along the length of the finger extensions.

While not specifically illustrated in FIG. 3A-3B, the electrochemical sensor may also include a reagent layer that immobilizes a suitable reagent near the working electrode 320 so as to sensitize the electrochemical sensor to one or more analytes. In some examples, this reagent layer takes the form of a permeable polymer layer disposed on the working electrode in the channel 350 positioned to expose the electrochemical sensor electrodes 320, 330 to a tear film. The reagent localized within the polymer layer may be comprised of a material configured to chemically react when proximate to an analyte. For example, the material may react to glucose in the tear film to which the sensor electrodes 320, 330 are exposed, creating a chemical by-product. In some examples, the reagent layer takes the form of a reagent deposited on the working electrode in the channel 350 positioned to expose the sensor electrodes 320, 330 to the tear film, where the deposited reagent is crosslinked by a crosslinking agent. In some examples, the sensor electrodes 320, 330 comprise a material sensitive to the chemical by-product, e.g. hydrogen peroxide, which may be sensed amperometrically by applying a voltage to the working electrode 320 relative to the reference electrode 330 and then measuring the current through the working electrode 320. The embodiments above are meant only as illustrative examples; other polymer layer compositions, crosslinking agents, reagents, electrode materials, and amperometric voltages are contemplated herein.

Figure 4A:
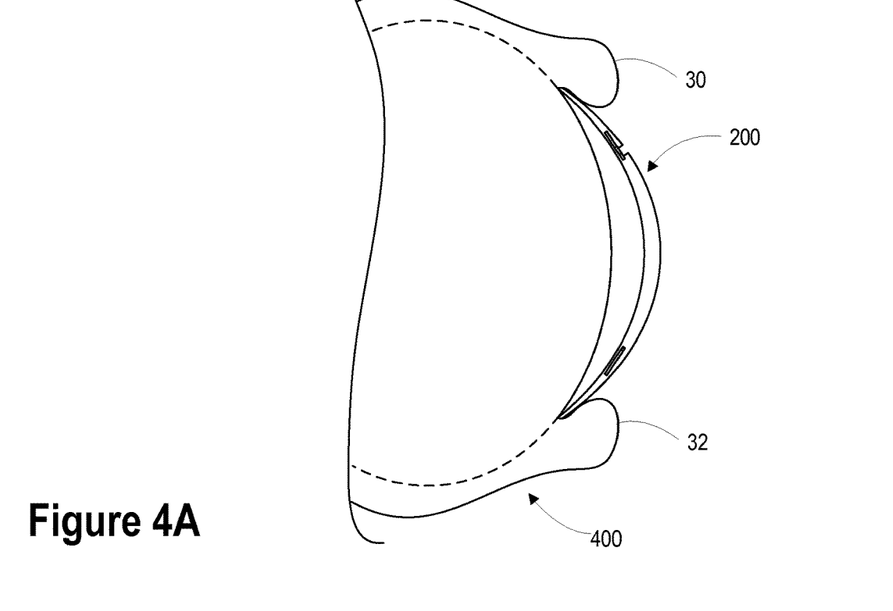
FIG. 4A illustrates a side cross-section view of an example eye-mountable device while mounted to a corneal surface of an eye with eyelids in an open position according to an example embodiment.
Figure 4B:
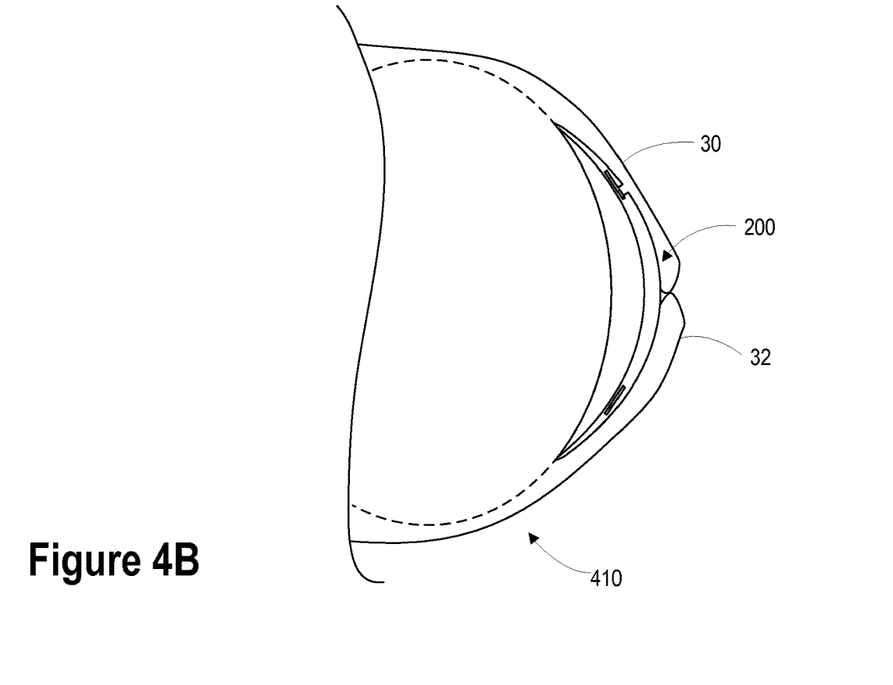
FIG. 4B illustrates a side cross-section view of an example eye-mountable device while mounted to a corneal surface of an eye with eyelids in a closed position according to an example embodiment.

FIGS. 4A and 4B illustrate side cross-section views of an example eye-mountable device. Specifically, FIGS. 4A and 4B show the eye-mountable device 200 while mounted to a corneal surface of an eye with eyelids in an open position 400 and a closed position 410. While the eyelids 30, 32 of an eye are in an open position 400, a mutual capacitance between two electrodes of a capacitance sensor (e.g. capacitance sensor 166) of the eye-mountable device 200 may be a first capacitance. While the eyelids 30, 32 of an eye are in a closed position 410, the mutual capacitance between the two electrodes of the capacitance sensor of the eye-mountable device may be a second capacitance. Furthermore, the mutual capacitance between the electrodes of the capacitance sensor may be related to a position of, or relative position between, upper eyelid 30 and lower eyelid 32. As such, an eyelid position may be determined based on the mutual capacitance between the electrodes of the capacitance sensor.

One or more devices or components described herein may be configured to sense a capacitance. For example, the controller 150 and/or the sensor interface 152 may be configured to record data indicative of the mutual capacitance between the electrodes of the capacitance sensor. The mutual capacitance may be sampled at periodic intervals, e.g. every 100 milliseconds, or at specified times.

In an example embodiment, the controller 150 and/or the sensor interface 152 may receive data indicative of the mutual capacitance at periodic intervals. In such a scenario, a first sample value of the mutual capacitance may indicate the first capacitance (open eyelids). Subsequently, a second sample value of the mutual capacitance may indicate the second capacitance (closed eyelids). Based on the difference between the first capacitance and the second capacitance being greater than a predetermined threshold or predetermined range, the controller 150 may detect an eye-related movement.

In an example embodiment, the controller 150 may be configured to carry out a calibration procedure. For example, the calibration procedure may include measuring a first capacitance value while an eyelid is at a first position, measuring a second capacitance value while the eyelid is at a second position, and determining the predetermined threshold based on a difference between the first capacitance value and the second capacitance value. Other calibration procedures are contemplated so as to determine the predetermined threshold.

While FIGS. 4A and 4B illustrate respective scenarios where the eyelids 30, 32 are open and closed, it is understood that other eyelid positions are possible within the context of this disclosure. For example, an intermediate capacitance value (e.g. between the first capacitance and the second capacitance) may indicate a partially-open eyelid position. Accordingly, controller 150 may be configured to determine an eye-related movement based on mutual capacitance values other than those while eyelids are fully open or fully closed.

Furthermore, the controller 150 may be configured to detect a variety of eye-related movements. For example, an eye-related movement may include, but is not limited to, a blink, a wink, an eye moving with respect to an eyelid, an eyelid moving with respect to the capacitance sensor, an eyelid closing, an eyelid opening, and/or a performance of any of the above movements in combination, in a predetermined pattern, and/or at a predetermined rate. Thus, detecting the eye-related movement may include the controller 150 receiving data indicative of a change in capacitance or data indicative of a predetermined pattern of changes in capacitance.

In response to detecting the eye-related movement, the controller 150 may produce a signal. The signal may trigger a notification and/or a dismissal of a notification. The signal may additionally or alternatively trigger a sample of the electrochemical sensor so as to detect a current concentration of an analyte. The signal may trigger other types of functions or dismissal/stoppage of such functions. For example, the signal may cause the controller 150 and/or the display driver 154 to illuminate the light source 162 based on an analyte level. Additionally or alternatively, the signal may trigger an indication of moisture level in the eye.

Method Examples

Figure 5:
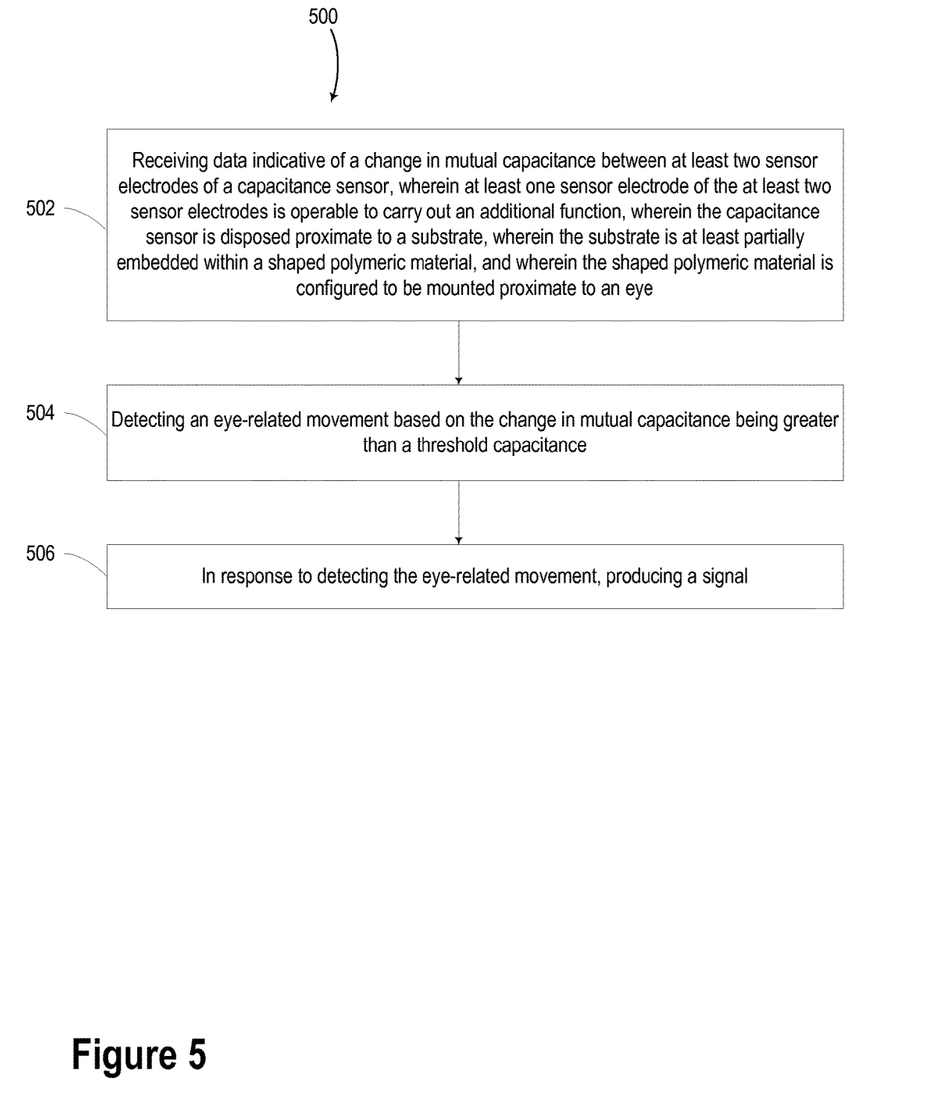
FIG. 5 is a flowchart illustrating a method according to an example embodiment.

FIG. 5 illustrates a method 500, according to an embodiment. The method 500 includes blocks that may be carried out in any order. Furthermore, various blocks may be added to or subtracted from method 500 within the intended scope of this disclosure. The method 500 may correspond to steps that may be carried out using any or all of the systems illustrated and described in reference to FIGS. 1, 2A, 2B, 2C, 2D, 3A, 3B, 4A, and 4B.

Block 502 includes receiving data indicative of a change in mutual capacitance between at least two sensor electrodes of a capacitance sensor. At least one sensor electrode of the at least two sensor electrodes may be operable to carry out an additional function. For instance, the at least one sensor electrode may be operable to sense an analyte and/or provide wireless communication. As an example, at least one sensor electrode of the capacitance sensor may include a working electrode or a reference electrode of an electrochemical sensor, such as sensor 166 illustrated and described in reference to FIG. 1. The capacitance sensor is disposed proximate to a substrate. The substrate is at least partially embedded within a shaped polymeric material. The shaped polymeric material is configured to be mounted proximate to an eye. The capacitance sensor, substrate, and shaped polymeric material may be similar or identical to corresponding elements of eye-mountable device 110 as illustrated and described in reference to FIG. 1.

Block 504 includes detecting an eye-related movement based on the change in mutual capacitance being greater than a threshold capacitance. The detecting may be performed by controller 150, which may occur when a difference between sampled capacitance values is greater than the threshold capacitance.

Block 506 includes producing a signal in response to detecting the eye-related movement. In other words, if a difference between sampled capacitance values is greater than the threshold capacitance, the controller 150 may produce a signal. As described elsewhere herein, the signal may trigger a notification or a dismissal of a notification. The signal may trigger (e.g. start, adjust, or stop) other functions of the eye-mountable device as contemplated herein.

As described elsewhere herein, the at least two sensor electrodes of the capacitance sensor may include a working electrode and a reference electrode. In such a scenario, the method may optionally include applying a voltage between the working electrode and the reference electrode so as to generate a current through the working electrode. The current may be related to oxidation or reduction of an analyte (e.g. glucose). The method may further include determining a concentration of the analyte based on the current through the working electrode. The method may also include providing an indication based on the concentration of the analyte. Furthermore, the method may include, in response to the signal, dismissing the indication.

As disclosed herein, a light source may be disposed proximate the substrate of the eye-mountable device. As such, the method optionally includes providing the indication using the light source.

In example embodiments, the light source may be controlled to perform several different indication functions. For example, in response to detecting the eye-related movement, the light source may be controlled to provide an indication visible to the wearer of the eye-mountable device. Alternatively or additionally, an existing indication may be stopped, e.g. by causing the light source to stop emitting light. For example, in response to detecting the eye-related movement, the light source may be controlled to stop the indication temporarily (e.g. "snooze" for five minutes or one hour) or permanently (e.g. until a new or different type of indication is presented). In other words, indications such as alerts or notifications may be dismissed or canceled for a given temporary duration, similar to a "snooze" button on an alarm clock. Subsequent to waiting for the temporary duration, the indications may be reasserted via the light source. Alternatively or additionally, the eye-related movement may permanently stop current indications until a new or different indication scenario arises.

The indication may include a temporally-varying intensity pattern or a constant intensity pattern. For example, the indication may include the light source providing a blinking indication, e.g. 1 Hz with 50% duty cycle. Additionally or alternatively, the indication may include the light source providing a slow blink, e.g. 0.2 Hz with 20% duty cycle. Other intensity patterns are possible. For example, the light source may be configured to provide an indication by varying an intensity of emitted light. In such a scenario, a "bright" indication may represent an analyte level being higher than a threshold and a "dim" indication may represent the analyte level being lower than a threshold.

Additionally or alternatively, as described herein, the eye-mountable device may include a plurality of light sources. Each of the plurality of light sources may be located in different locations proximate to the eye-mountable device. In such a scenario, the indications may include illuminating the light sources in a spatially-varying manner. For example, a first indication may include illuminating the plurality of light sources at the same time in a simultaneous blinking fashion. A second indication may include illuminating each of the plurality of light sources at different times. Other ways to provide and control visual indications about a wearable computing system in response to detecting an eye-related movement are contemplated herein.

In some embodiments, the at least two sensor electrodes may be disposed in an interdigitated arrangement. Furthermore, at least one of the at least two sensor electrodes of the capacitance sensor may optionally be communicatively coupled to at least a portion of an antenna. For example, a first sensor electrode of the capacitance sensor may include the antenna and a second sensor electrode may include one of the working electrode or the reference electrode of an electrochemical sensor. The capacitance sensor may include other sensor electrodes operable to carry out other additional functions.

The method optionally includes providing a calibration procedure. The calibration procedure includes measuring a first capacitance value using the capacitance sensor while an eyelid is at a first position, measuring a second capacitance value using the capacitance sensor while the eyelid is at a second position, and determining the predetermined threshold based on a difference between the first capacitance value and the second capacitance value.

In some embodiments, the eye-related movement may include at least one of: a blink, a wink, an eye moving with respect to an eyelid, an eyelid moving with respect to the capacitance sensor, and an eyelid closing. Other eyelid movements are possible.

The method optionally includes, in response to detecting the eye-related movement, causing the capacitance sensor to measure the concentration of the analyte.

The particular arrangements shown in the Figures should not be viewed as limiting. It should be understood that other embodiments may include more or less of each element shown in a given Figure. Further, some of the illustrated elements may be combined or omitted. Yet further, an illustrative embodiment may include elements that are not illustrated in the Figures.

While various examples and embodiments have been disclosed, other examples and embodiments will be apparent to those skilled in the art. The various disclosed examples and embodiments are for purposes of illustration and are not intended to be limiting, with the true scope being indicated by the following claims.

What is claimed is:

1. An eye-mountable device comprising:
a substrate, wherein the substrate is at least partially embedded within a shaped polymeric material;
a capacitance sensor disposed proximate to the substrate, wherein the capacitance sensor comprises at least two sensor electrodes, wherein at least one sensor electrode of the at least two sensor electrodes is operable to carry out an additional function, wherein the at least two sensor electrodes comprise a working electrode and a reference electrode, wherein the additional function comprises sensing an analyte; and
a controller disposed proximate to the substrate and communicatively coupled to the at least two sensor electrodes, wherein the controller is configured to:
apply a voltage between the working electrode and the reference electrode so as to generate a current through the working electrode;
determine a concentration of the analyte based on the current through the working electrode;
receive data indicative of a change in mutual capacitance between the at least two sensor electrodes;
detect an eye-related movement based on the change in mutual capacitance being greater than a threshold capacitance; and
in response to detecting the eye-related movement, produce a signal.

2. The eye-mountable device of claim 1, wherein the controller is further configured to:
provide an indication based on the concentration of the analyte; and
in response to the signal, dismiss the indication.

3. The eye-mountable device of claim 1, wherein the analyte is glucose.

4. The eye-mountable device of claim 1, further comprising a light source disposed proximate the substrate.

5. The eye-mountable device of claim 4, wherein the controller is further configured to, in response to detecting the eye-related movement, perform at least one of: causing the light source to provide an indication, stopping the indication temporarily, or stopping the indication permanently.

6. The eye-mountable device of claim 1, wherein the working electrode and the reference electrode are disposed proximate to a channel configured to contain tear fluid from an eye.

7. The eye-mountable device of claim 1, wherein the at least two sensor electrodes are in an interdigitated arrangement.

8. The eye-mountable device of claim 1, wherein at least one of the at least two sensor electrodes comprises at least a portion of an antenna, and wherein the additional function comprises wireless communication.

9. The eye-mountable device of claim 1, wherein the controller is further configured to provide a calibration procedure, wherein the calibration procedure comprises:
measuring a first capacitance value using the capacitance sensor while an eyelid is at a first position;
measuring a second capacitance value using the capacitance sensor while the eyelid is at a second position; and
determining the threshold capacitance based on a difference between the first capacitance value and the second capacitance value.

10. The eye-mountable device of claim 1, wherein the eye-related movement comprises at least one of: a blink, a wink, an eye moving with respect to an eyelid, an eyelid moving with respect to the capacitance sensor, and an eyelid closing.

11. The eye-mountable device of claim 1, wherein the controller is further configured to, in response to detecting the eye-related movement, cause the capacitance sensor to measure the concentration of the analyte.

12. The eye-mountable device of claim 1, wherein detecting the eye-related movement further comprises receiving data indicative of a predetermined pattern of changes in mutual capacitance between the at least two sensor electrodes.

* * * * *